Figure 1:
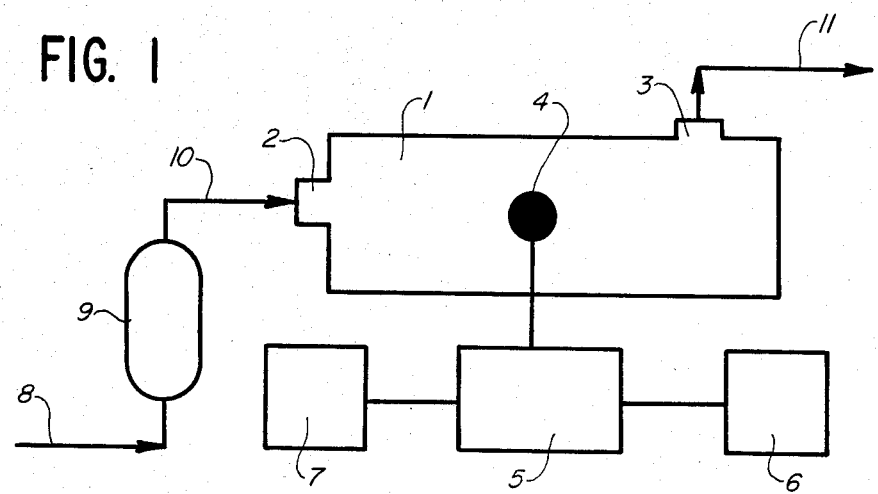

United States Patent [19]

Minten et al.

[11] Patent Number: 4,637,987

[45] Date of Patent: * Jan. 20, 1987

[54] GAS MONITORING DEVICE AND METHOD

[75] Inventors: Karl Minten, La Hoya, Calif.; William Krug, Hoffman Estates, Ill.

[73] Assignee: Gould Inc., Rolling Meadows, Ill.

[ * ] Notice: The portion of the term of this patent subsequent to Oct. 1, 2002 has been disclaimed.

[21] Appl. No.: 607,514

[22] Filed: May 7, 1984

[51] Int. Cl.$^4$ ................... G01N 27/00; G01N 31/00
[52] U.S. Cl. ........................... 436/151; 73/23; 73/DIG. 4; 422/88; 422/98; 436/136; 436/167
[58] Field of Search ............... 436/151, 164, 167; 422/69, 56, 57, 86, 87, 88, 90, 91, 98; 260/429 R; 73/23, DIG. 4

[56] References Cited

U.S. PATENT DOCUMENTS

| | | | |
|---|---|---|---|
| 2,232,622 | 2/1941 | Moses et al. | 23/255 |
| 2,741,544 | 4/1956 | Chaikin et al. | 23/255 |
| 2,800,397 | 7/1957 | Offutt et al. | 23/232 |
| 2,895,807 | 7/1959 | Sorg et al. | 23/255 |
| 3,114,610 | 12/1963 | Gafford et al. | 23/255 |
| 3,164,004 | 1/1965 | King, Jr. | 73/23 |
| 3,194,053 | 7/1965 | Shang | 73/23 |
| 3,260,104 | 7/1966 | King, Jr. | 73/23 |
| 3,329,004 | 7/1967 | King, Jr. | 422/98 X |
| 3,343,044 | 9/1967 | King, Jr. et al. | 317/146 |
| 3,538,133 | 11/1970 | Knoth, Jr. | 260/429 |
| 3,694,164 | 9/1972 | Guenther | 422/88 X |
| 3,744,296 | 7/1973 | Beltzer | 73/23 |
| 3,754,867 | 8/1973 | Guenther | 23/254 R |
| 3,870,469 | 3/1975 | Walker | 23/232 E |
| 4,027,084 | 5/1977 | Tkatchenko | 526/27 |
| 4,032,297 | 6/1977 | Lyshkow | 23/254 E |
| 4,032,617 | 6/1977 | Gay | 423/219 |
| 4,042,333 | 8/1977 | Dell et al. | 23/232 R |
| 4,081,769 | 3/1978 | Shreve | 333/72 |
| 4,096,740 | 6/1978 | Sallee . | |
| 4,100,811 | 7/1978 | Callen et al. | 73/654 |
| 4,111,036 | 9/1978 | Frechette et al. | 73/23 |
| 4,230,828 | 10/1980 | Gaul, Jr. et al. | 525/153 |
| 4,251,452 | 2/1981 | McAuliffe et al. | 260/429 R |
| 4,312,228 | 1/1982 | Wohltjen | 73/597 |
| 4,313,338 | 2/1982 | Abe et al. | 73/23 |
| 4,323,543 | 4/1982 | McAuliffe et al. | 423/219 |
| 4,343,715 | 8/1982 | Bonaventura et al. | 252/186 |
| 4,361,026 | 11/1982 | Muller et al. | 73/23 |
| 4,442,297 | 4/1984 | Hill et al. | 260/429 R X |

OTHER PUBLICATIONS

Hlavay et al., Analytical Chemistry, vol. 49, No. 13, Nov. 1977, pp. 1890–1898.

Hosseiny et al., Inorganic Chimica Acta, 39 (1980) 227–231.

Janata et al, "Ion Selective Electrodes" in Freiser (ed), Analytical Chemistry, vol. 2, pp. 124–126 (1980).

Garverick et al, IEEE Trans. Electron Dev., vol. 29, pp. 90–94 (1982).

Mins, III–Engineer's Notebook II, p. 87 (1982).

Clark, Jr., Trans. Amer. Soc. Artif. Intern. Organs, vol. 2, pp. 41–48 (1956).

Babmet et al, Anal. Chem. vol. 43, pp. 803–805 (1971).

Hersch, Amer. Lab. (Aug. 1983), pp. 29–36.

McAuliffe et al, "Working Haem Analogues; Reversible Oxygenation of the Manganese-Tertiary Phosphine Complexes $MnLX_2$", JCS Chemical Communications 1979, pp. 736–738 (1979).

Primary Examiner—Arnold Turk
Attorney, Agent, or Firm—J. M. Walder; G. P. Edgell; E. E. Sachs

[57] ABSTRACT

Method and apparatus which can provide continuous monitoring of the partial pressure of one or more gases in an atmosphere or feed stream, over an indefinite period of time and at a minimal cost. The method and apparatus of the present invention operates by monitoring the change in frequency of a piezoelectric element which has been coated with a film formed from manganese tertiary phosphine polymer complex. As the polymer absorbs or releases gas the frequency of the piezoelectric device will be altered.

25 Claims, 3 Drawing Figures

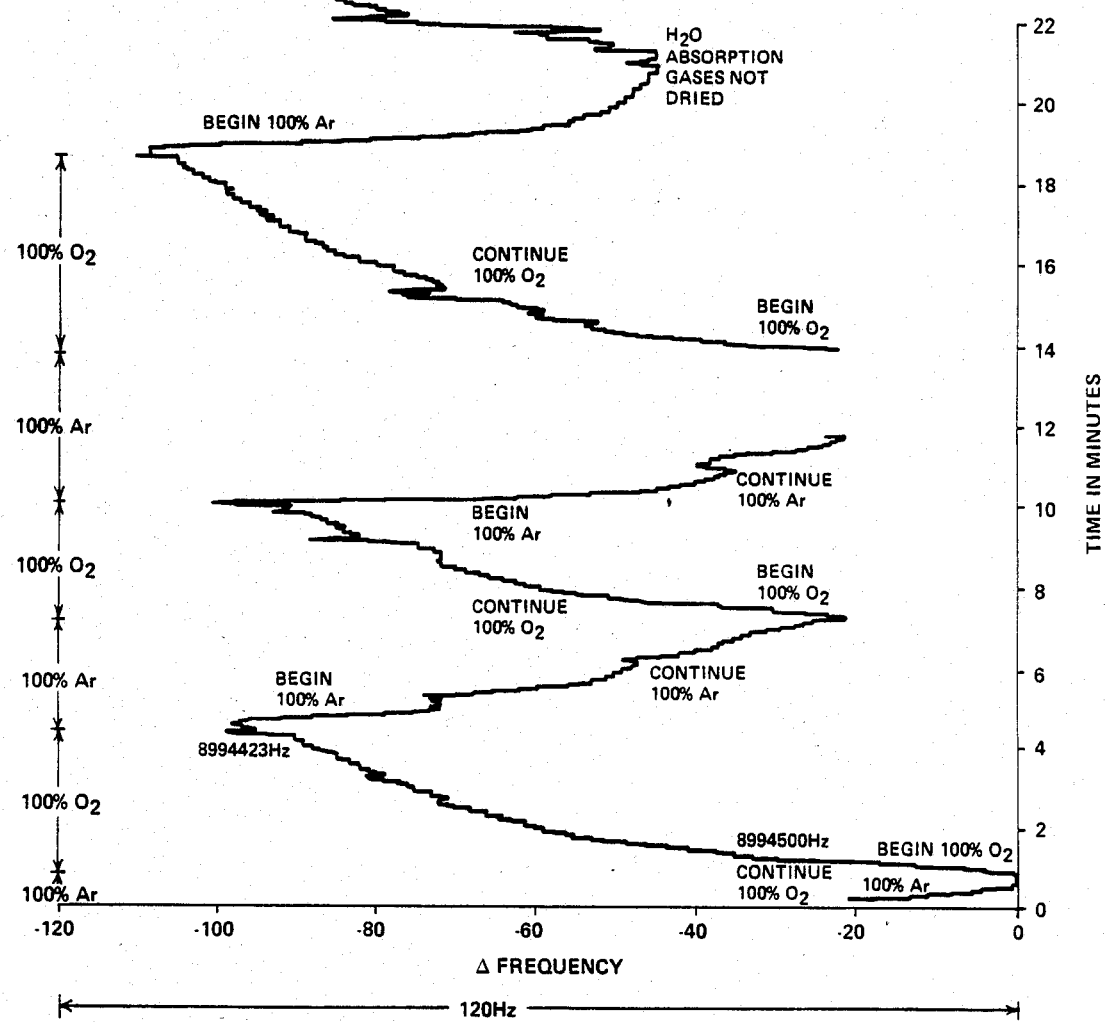

GAS MONITORING DEVICE AND METHOD

BACKGROUND OF THE INVENTION

The present invention relates to a novel method and apparatus for monitoring the level of oxygen in a feed stream or within the atmosphere of a defined space such as an oxygen chamber, oxygen tent, a room, or the like.

In the past there have been a number of procedures and apparatus proposed for the monitoring or analysis or sampling of gases. These include electrochemical methods, mass spectrometry methods, CHEMFET devices, charger flow transistors, gas chromatographic and other colorimetric procedures. In general, these involved extremely expensive and sophisticated equipment and techniques or mechanisms which were not truly reversible and/or indefinitely continuous. In most cases, they relied on a chemical reaction by the gas which would provide a corresponding change in pH thereby triggering a color change in an indicator as a colorimetric chemical reaction which was not quickly and fully reversible. Also, such systems are obviously subject to the vagaries of other gases which might be present particularly the relative amount of humidity present.

The earliest systems for monitoring of gases generally related to gases such as carbon dioxide, hydrogen sulfide, halogens and the like. These systems were colorimetric in nature, but the colorimetric reaction was not immediately and completely self reversing in response to a reversal of the change in concentration of the gas being monitored.

As examples of one type of system taught by the prior art, mention might be made of U.S. Pat. No. 3,754,867 to Karl R. Guenther, in which the carbon dioxide content of ambient air is monitored using a thin layer of chemical which will absorb carbon dioxide forming an acid which will provide a change in pH. An indicator present in the film changes color. The system circumvents problems of humidity by using an ionizing solvent having a vapor pressure in the range of 0-10 mm at temperatures up to 150° F., and compatible with the other components of the system.

Another method is proposed by U.S. Pat. No. 3,114,610 to Gafford et al, using very sophisicated analyzing equipment to measure the particular presence of a constituent of a gas, which constituent produces acidic or basic solutions. Again, basically a one-way system in which the sample must be either neutralized, or the indicator replaced, or the instrument recalibrated before further sampling can continue.

U.S. Pat. No. 2,232,622 to Moses et al and U.S. Pat. No. 2,741,544 to Chaikin et al provide an alternate method in which continuous sampling is possible over a finite period of time. Moses et al relates to the monitoring of hydrogen sulfide, and Chaiken et al relates to an apparatus for fluoride analysis. They are, however, very similar methods, in that continuous analysis over a finite period of time is achieved by winding forward a continuous strip of tape impregnated with the indicator. As with Guenther and Gafford, however, the system relies on a change in pH to trigger a color change in an indicator.

All of the foregoing systems have certain basic limitations. They can only measure gases which provide an acidic or basic solution such as carbon dioxide, hydrogen sulfide, halogen, or the like; and they are operable, at best, intermittently or over a relatively finite period of time. In addition, those which do provide for some measure of continuous monitoring, such as Moses et al, involve very cumbersome and relatively expensive apparatus, such as a drive motor and the like.

The range of oxygen detection methods is large but generally very sophisticated and more expensive than those described above and includes such diverse means as electrochemical reactions and cells, optical fiber monitors based on fluorescence quenching of dyes or colorimetric oxygen reactions, CHEMFETS and charge-flow transistor devices, anaerobic bacterial activity, mass spectrometry, gas chromatography and the addition of odorants of other detectable trace gas additives to the oxygen supply. However, use of most such techniques is far from commercialization, while others are suitable only for certain limited applications. None of these techniques provide an inexpensive continuous simple procedure for in-line monitoring of oxygen level in a fuel stream or enclosed area.

The Clark cell [L. C. Clark, Jr., *Trans. Amer. Soc. Artif. Intern. Organs,* 2, 41–48 (1956)] is the most commonly used electrometric oxygen sensor available today. It is based on polarographic principles by which, for a given applied voltage, the current between two electrodes is directly proportional to the oxygen partial pressure in the environment.

A very similar polarographic monitor has also been developed by Hersch [W. Bahmet and P. A. Hersch, *Anal. Chem.,* 43, 803 (1971) and P. A. Hersch, *Amer. Lab,* Aug. 1973, p. 29] and is based on the linear variation of the limiting current attainable from a cadmium-air cell when the partial pressure of oxygen is varied. There are two very major problems with such electrochemical methods, since they depend on the precise maintenance of solution concentration, and they depend upon a kinetically limited gas/liquid equilibrium system. One can speculate optical methods since these methods could theoretically be based on any colorimetric oxygen reaction.

Mass spectrometry and gas chromatography, however, are the methods conventionally used for the quantitative and qualitative analysis of gases, and could easily be adapted to oxygen monitoring. A major consideration in their use, however, would be their relative cost and size. A detector based specifically on the paramagnetic properties of oxygen is also conceivable, but seems even less promising than mass spectrometry or gas chromatography on the basis of cost, size and versatility. Thus, simple optical systems are purely speculative, while instrumental procedures are too complex and too expensive.

Transistor devices have also been suggested. CHEMFET devices have been proposed for monitoring systems. Use of these chemically sensitive field effect transistor devices [J. Janata and R. H. Huber, in "Ion-Selective Electrodes", *Analytical Chemistry,* Vol. 2, H. Frieser, ed., Plenum Press, New York, 1980, pp. 124–6] is predicated on the measurement of changes in the source/drain current passing through a transistor due to variations in the electric field in the gate region of the device. The observed changes in current could, for example, result from the absorption of oxygen on, or its reaction with, material in the gate region of the device.

Charge-flow transistors have also been suggested. Application of these devices [S. L. Garverick and S. D. Senturia, *IEEE Trans. Electron Dev.,* 29, 90 (1982)] involves the measurement of the change in admittance (AC conductance) of a transistor resulting from the adsorption of a given species (e.g. $O_2$) on, or its reaction with, a resistive material placed in the gate region of the device. The admittance of the device is directly related to the time delay observed between the application of a gate-to-source voltage and the initiation of the source-to-drain current. Both CHEMFET devices and charge-flow transistors tend to be very complex systems overall, and yet are very unreliable.

In an article by Hlavay and Guilbault entitled "Applications of the Piezoelectric Crystal Detector in Analytical Chemistry", *Analytical Chemistry,* Vol 49, No. 13, November 1977, the use of a piezoelectric device and an absorption coating to measure gas concentration is discussed. The article notes that as gas is absorbed there is a frequency change in the quartz crystal which can be measured. The noted materials range from various absorption polymers, to waxes, alcohols, and amines. The article indicates difficulty in obtaining reproducible results because of the nature of the coating materials. Also, the discussion deals with absorbing only since the system disclosed by Hlavay and Guilbault is not reversible, and is not adaptable to continuous monitor changes where the partial pressure of the gas being measured may rise or fall. The article does, however, discuss specific teaching for the handling, disposition, and calibration of coated crystal sensing devices, many of which could be adapted for use in the present invention.

None of the teachings heretofore available provide a truly inexpensive and completely reliable apparatus and/or method by which the oxygen content of a gas or atmosphere can be continuously and reversibly monitored over an indefinite period of time using non-depletable materials and, insofar as the monitoring element, no moving parts.

It will be appreciated that a serious need exists to monitor not only the oxygen content of a gas feed stream or the atmosphere within a container, chamber, room, or the like, but advantageously a number of such gases, and particularly the relative content of a number of such gases in a mixed feed stream to maintain continuous monitoring with instantaneous warning in the event of an undue pressure change of one or more constituents. Such systems and apparatus would have particular utility and applicability in medical applications, such as monitoring the oxygen feed to a patient and/or the oxygen content of the atmosphere within an oxygen tent or room. Such monitoring is now possible, if at all, only using extremely cumbersome and expensive equipment.

IN THE DRAWINGS

FIG. 1 is a schematic illustration of one embodiment of the present invention.

Figure 2:
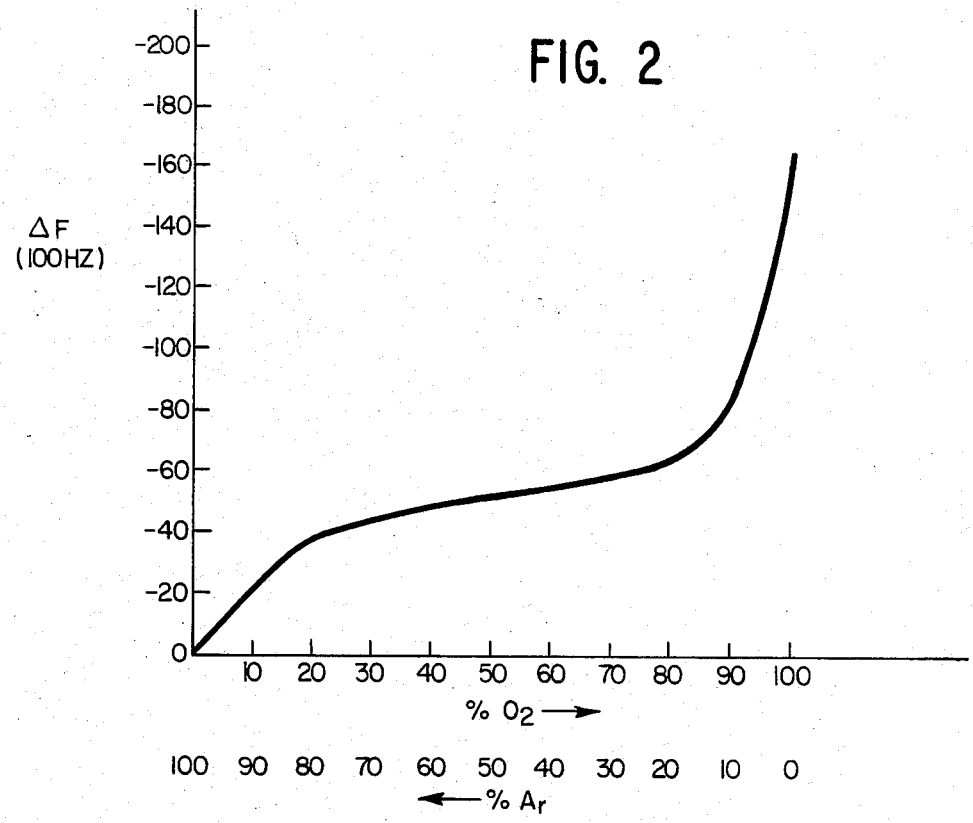

FIG. 2 graphically displays the change in frequency at varying gas partial pressures.

FIG. 3 shows frequency changes as gas is reversibly absorbed and desorbed.

SUMMARY OF INVENTION

We have now discovered a novel method and apparatus which can provide continuous monitoring of the partial pressure of one or more gases in an atmosphere or feed stream, over an indefinite period of time and at a minimal cost. The method and apparatus of our invention provides a prompt response to critical changes in pressure level of a given gas independent of the level of humidity, and without the need for the use of pH sensitive indicators, or expensive and sophisticated analytical instruments.

The basic mechanism of the present invention for mearsuring the change in partial pressure of a gas being monitored, is the change in frequency of a piezoelectric element which has been coated with a film formed from manganese tertiary phosphine polymer complex. As the polymer absorbs or releases gas the frequency of the piezoelectric device is altered. The relationship between the mass deposited and the change in vibrational frequency is:

$$\Delta F = -2.3 \times 10^{-6} F^2 \frac{\Delta W}{A}$$

$\Delta F$ = Frequency change (Hz)
$F$ = Fundamental of crystal (mHz)
$\Delta W$ = Change in mass of crystal due to deposit (g)
$A$ = Area coated by film (cm$^2$)

If such a crystal was coated with a film from manganese thiocyanate-tri-n-butyl phosphine-PVC-THF complex, for example the change in frequency due to the absorption or desorption of co-ordinated $O_2$ could be followed as a function of the frequency of the crystal.

By measuring the change in frequency it would be possible to continuously monitor the ambient pressure of oxygen or any given gas and/or provide for an alert in the event that the pressure of a given gas becomes higher or lower than some predetermined upper or lower limit.

Applicants' copending, commonly assigned applications Ser. Nos. 607,513 and 607,512 filed May 7, 1984 (the specifications and claims of which are specifically incorporated herein by reference) disclose and claims respectively, certain novel manganese tertiary phosphine polymer complexes, and the use of a change in color intensity of films formed from such complexes to monitor oxygen content of a gas stream.

The manganese tertiary phosphine polymer complexes are prepared by adding a manganese salt to an anhydrous solution of a polymer selected from the group consisting of polyvinylchloride, silicone, polyvinylacetate, and polystyrene, in a suitable solvent, then adding a monodentate ligand to the polymer-manganese salt solution. These polymer compositions will reversibly complex with gases such as oxygen, hydrogen, sulfur dioxide, alkenes, carbon monoxide and the like. The manganese salt corresponds to the formula:

wherein X is a species capable of forming an anion; and the ligand is a compound of the formula:

wherein $R^1$, $R^2$, and $R^3$ may be the same or different, and is selected from the group consisting of substituted or unsubstituted alkyl, cycloalkyl or aryl groups or hydrogen, provided that at least one of the groups $R^1$, $R^2$, and $R^3$ is a substituted or unsubstituted alkyl, cycloalkyl or aryl group.

While elevated temperatures may be required to dissolved the starting polymer in the solvent such as tetrahydrofuran the remainder of the synthesis can generally be carried out at room temperature, though preferably under anhydrous conditions. The polymer content of the starting polymer solution can vary widely and is primarily dependent on the amount of solvent needed to maintain suitable handling conditions such as any desired vicosity or the like. A 2% to 30% by weight solution is generally considered operable, and a 5% to 20% by weight solution is preferred.

The weight ratio of manganese salt to starting polymer is usually in the range of about 1:10 to 2:1 and preferably about 1:2 to 2:1. The ligand is added as at least a stoichiometric equivalent of the manganese salt, and preferably as a stoichiometric excess of 50% to 150%.

Ligands of particular interest includes those within the following groups:

Phenyldialkylphosphines, diphenylalkylphosphines, cyclohexyldialkylphosphines, dicyclohexylalkylphosphines, trialkylphosphines, including methyldialkylphosphines, ethyldialkylphosphines, pentyldialkylphosphines, octyldialkylphosphines, and dodecyldialkylphosphines. The following specific ligands are generally regarded as of interest, trimethylphosphine, triethylphosphine, tributylphosphine, methyldiethylphosphine, ethyldimethylphosphine, dimethylphenylphosphine, diethylphenylphosphine, methyldiphenylphosphine, diphenylethylphosphine, trioctylphosphine, in which the alkyl group is preferably a straight chain alkyl group.

A film can be cast from the solution of the polymer composition by any of a variety of widely known techniques well known to those skilled in the art. As taught by McAuliffe [J.C.S. Chem. Comm. 1979, pp. 736–738; U.S. Pat. Nos. 4,251,452 and 4,323,543], by selecting a particular ligand it is possible to control the selection of the specific gas which will be complexed. By using a plurality of piezoelectric devices coated with films formed from different complexes, it is possible to monitor a plurality of gases. Then, as the pressure of a given gas rises or falls, the gas in question will be absorbed by, or released from, the corresponding film thereby causing a measurable change in the frequency of the particular piezoelectric sensor.

FIG. 1 is a schematic illustration of one embodiment of the present invention wherein a gas is passed into a defined enclosed area 1 having input means 2 and egress means 3, and having disposed within said area a piezoelectric crystal 4 coated with a film produced from a manganese tertiary phosphine polymer complex. The preferred method for coating the film onto a crystal is by means of standard dip coating techniques. The piezoelectric device 4 is connected to an oscillator 5 which may be connected to suitable related means such as recording means 6 and/or a power supply 7. A stream of gas is fed through means feed 8 to metering means 9 through connecting means 10 to input means 2. Exit feed 11 is connected to egress means 3. In fact, gas feed means 8 may comprise a plurality of feed means for individual gasses and metering means 9 will normally consist of one metering device for each separate gas feed line. Metering means 9 provides the desired feed mix through line 10 to the piezoelectric device 4.

The following specific example will show by way of illustration and not by way of limitation, the use of the novel method and apparatus of the present invention.

EXAMPLE

A device was constructed based on the schematic diagram illustrated in FIG. 1. Oxygen and argon were fed to a pair of flow meters and the mixed feed was fed to an enclosed chamber in which a piezoelectric crystal was disposed. The quartz crystal had been dip coated with manganese thiocyanate-n-tributyl phosphine-THF-PVC complex. The crystal was connected to an oscillator which in turn was connected to a Hewlett Packard 6234 power supply device, and a Hewlett Packard 5302 50 mHz Frequency Counter. The metering devices were used to vary the percent of oxygen in the feed stream. FIG. 2 illustrates the change in frequency of the piezoelectric device as the oxygen partial pressure was varied and FIG. 3 illustrates the change in frequency over a series of cycles, as the oxygen pressure was first increased and subsequently reduced. In general, in the course of these experiments the equilibration period was about three minutes though this could be substantially shortened by chosing a different ligand or varying the thickness of the film.

Similar experiments were conducted with manganese thiocyanate tri-n-butyl phosphine-THF-PVC in measuring oxygen partial pressure. It is possible to obtain a similar measurement for carbon dioxide employing manganese chloride tri-n-propyl phosphine-THF-PVC.

As noted above, McAuliffe et al, teach that by varying the ligand it is possible to selectively absorb a variety of other gases.

It would be obvious that the embodiment illustrated by FIG. 1 is just that, one embodiment. The above noted by Hlavay and Guilbault suggests certain alternative arrangements for the disposition and calibration of a coated piezoelectric device which should be adaptable for use in the practice of the present invention.

It will of course also be obvious that other changes, modifications and alterations can be made in the compositions and methods herein described without departing from the scope of the invention herein disclosed and it is our intention to be limited only by the appended claims.

As our invention we claim:

1. Apparatus for monitoring the concentration of at least one gas in a feed stream; comprising means defining an enclosed area wherein said gas is to be contained; a piezoelectric device within said defined area having disposed on its surface a thin film formed from a manganese tertiary phosphine polymer complex; said piezoelectric device being suitably connected to measurement means whereby changes in frequency in the piezoelectric device can be recorded.

2. The apparatus according to claim 1 wherein the polymer in the complex is silicone.

3. The apparatus according to claim 1 wherein a plurality of piezoelectric devices is disposed within said area, each having a film cast from a different manganese tertiary phosphine polymer complex; each being suitably connected to measurement means.

4. The apparatus according to claim 1 wherein said polymer complex is produced by the steps which comprise: forming a substantially anhydrous first solution of a polymer selected from the group consisting of polyvinylchloride, polystyrene, polyvinylacetate, and silicone, dissolved in a suitable solvent; adding a substantially anhydrous manganese salt of the formula:

wherein X is a species capable of forming an anion to form a second solution; then adding to the solution of polymer and manganese salt at least a stoichiometric equivalent with respect to said manganese salt of a substantially anhydrous phosphine of the formula:

$PR^1R^2R^3$ wherein $R^1$, $R^2$, and $R^3$ may be the same or different, and each is selected from the group consisting of substituted or unsubstituted alkyl, cycloalkyl or aryl groups or hydrogen, provided that no more than two of the groups $R^1$, $R^2$, and $R^3$ are substituted or unsubstituted aryl groups and that at least one of the groups $R^1$, $R^2$, and $R^3$ is a substituted or unsubstituted alkyl, cycloalkyl or aryl group.

5. The apparatus according to claim 4 wherein X is a member selected from the group consisting of chlorine, bromine, iodine and thiocyanate, and said solvent is tetrahydrofuran.

6. The apparatus according to claim 4 wherein a stoichiometric excess of phosphine is employed.

7. The apparatus of claim 4 wherein said phosphine is selected from the group consisting of methyldialkylphosphines, ethyldialkylphosphines, and pentyldialkylphosphines.

8. The apparatus of claim 4 wherein said polymer comprises between about 2 and 30 wt.%, inclusive, of said first solution, the weight ratio of said manganese salt to said polymer is in the range of about 1:10 to 2:1, inclusive, and said phosphine is added to a stoichiometric excess with respect to said manganese salt of between about 50 to 150%, inclusive.

9. The apparatus of claim 8 wherein said polymer comprises between about 5 and 20 wt.%, inclusive, of said first solution and said weight ratio of said manganese salt to said polymer is between about 1:2 and 2:1, inclusive.

10. The apparatus according to claim 4 wherein said phosphine is selected from the group consisting of phenyldialkylphosphines, diphenylalkylphosphines, cyclohexyldialkylphosphines, dicyclohexylalkylphosphines, trialkylphosphines, octyldialkylphosphines, and dodecyldialkylphosphines.

11. The apparatus according to claim 10 wherein said phosphine is selected fron the group consisting of trimethylphosphine, triethylphosphine, tributylphosphine, methyldiethylphosphine, ethyldimethylphosphine, dimethylphenylphosphine, diethylphenylphosphine, methyldiphenylphosphine, diphenylethylphosphine, and trioctylphosphine.

12. The apparatus according to claim 10 wherein said polymer is polyvinylchloride.

13. A method of monitoring the partial pressure of at least one gas the steps which comprise; disposing a coating of a manganese tertiary phosphine polymer complex film on a piezolelectric crystal; disposing said crystal in a defined enclosed area in which the gas is to be contained; passing the gas through said area; attaching said piezoelectric crystal to measurement means whereby changes in frequency of the piezoelectric device can be recorded.

14. The method according to claim 13 where said polymer complex is synthesized by the steps which comprise: forming a substantially anhydrous first solution of a polymer selected from the group consisting of polyvinylchloride, polystyrene, polyvinylacetate, and silicone, dissolved in a suitable solvent; adding a substantially anhydrous manganese salt of the formula:

$MnX_2$ wherein X is a species capable of forming an anion to form a second solution; then adding to the solution of polymer and manganese salt at least a stoichiometric equivalent with respect to said manganese salt of a substantially anhydrous phosphine of the formula:

$PR^1R^2R^3$ wherein $R^1$, $R^2$, and $R^3$ may be the same or different, and each is selected from the group consisting of substituted or unsubstituted alkyl, cycloalkyl or aryl groups or hydrogen, provided that no more than two of the groups $R^1$, $R^2$, and $R^3$ are substituted or unsubstituted aryl groups and that at least one of the groups $R^1$, $R^2$, and $R^3$ is a substituted or unsubstituted alkyl, cycloalkyl or aryl group.

15. The method according to claim 14 wherein a plurality of piezoelectric devices is disposed within said area, each having a film cast from a different manganese tertiary phosphine polymer complex, each being suitably connected to measurement means.

16. The method of claim 14 wherein said phosphine is selected from the group consisting of methyldialkylphosphines, ethyldialkylphosphines, and pentyldialkylphosphines.

17. The method according to claim 14 wherein a stoichiometric excess of phosphine is employed.

18. The method according to claim 14 wherein the polymer in the complex is silicone.

19. The method according to claim 14 wherein said solvent is tetrahydrofuran.

20. The method according to claim 19 wherein X is a member selected from the group consisting of chlorine, bromine, iodine and thiocyanate.

21. The method of claim 14 wherein said polymer comprises between about 2 and 30 wt.%, inclusive, of said first solution, the weight ratio of said manganese salt to said polymer is in the range of about 1:10 to 2:1, inclusive, and said phosphine is added in a stoichiometric excess with respect to said manganese salt of between about 50 to 150%, inclusive.

22. The method of claim 21 wherein said polymer comprises between about 5 and 20 wt.%, inclusive, of said first solution and said weight ratio of said manganese salt to said polymer is between about 1:2 and 2:1, inclusive.

23. The method according to claim 14 wherein said phosphine is selected from the group consisting of phenyldialkylphosphines, diphenylalkylphosphines, cyclohexyldialkylphosphines, dicyclohexylalkylphosphines, trialkylphosphines, octyldialkylphosphines and dodecyldialkylphosphines.

24. The method according to claim 23 wherein said phosphine is selected from the group consisting of trimethylphosphine, triethylphosphine, tributylphosphine, methyldiethylphosphine, ethyldimethylphosphine, dimethylphenylphosphine, diethylphenylphosphine, methyldiphenylpospine, diphenylethylphosphine, and trioctylphosphine.

25. The method according to claim 23 wherein said polymer is polyvinylchloride.

* * * * *